United States Patent [19]

Ker et al.

[11] Patent Number: 4,824,550
[45] Date of Patent: Apr. 25, 1989

[54] HEATED SOLID ELECTROLYTE OXYGEN SENSOR AND SECURING ELEMENT THEREFOR

[75] Inventors: Eric L. Ker, Grand Blanc; Joseph R. Griffin, Fenton, both of Mich.

[73] Assignee: General Motors Corporation, Detroit, Mich.

[21] Appl. No.: 110,353

[22] Filed: Oct. 19, 1987

[51] Int. Cl.⁴ ............................................. G01N 27/58
[52] U.S. Cl. ................................... 204/427; 439/434; 439/444
[58] Field of Search ............... 204/427, 428, 429, 1 S; 439/444, 434

[56] References Cited

U.S. PATENT DOCUMENTS

| | | | |
|---|---|---|---|
| 3,686,609 | 8/1972 | Hansen | 439/444 X |
| 3,844,920 | 10/1974 | Burgett et al. | 204/428 |
| 4,175,019 | 11/1979 | Murphy | 204/429 |
| 4,540,479 | 9/1985 | Sakurai et al. | 204/427 |
| 4,578,174 | 3/1986 | Kato et al. | 204/429 |

Primary Examiner—G. L. Kaplan
Attorney, Agent, or Firm—Domenica N. S. Hartman

[57] ABSTRACT

A readily manufacturable heated solid electrolyte oxygen sensor. A heater subassembly readily adaptable to unheated oxygen sensor technology, provides the means for positioning and rigidly securing the heater element within the oxygen sensing device, while also providing the means for electrically coupling the galvanic output signal to the external combustion control system.

9 Claims, 1 Drawing Sheet

HEATED SOLID ELECTROLYTE OXYGEN SENSOR AND SECURING ELEMENT THEREFOR

The present invention generally relates to an electrochemical type solid electrolyte oxygen sensor suitable for detecting oxygen concentrations in automotive exhaust emitted from an internal combustion engine. More specifically, this invention relates to a self heating oxygen sensor of this type which is rugged, durable and readily assembleable.

BACKGROUND OF THE INVENTION

Gas sensors are employed in a variety of applications requiring qualitative and quantitative gaseous determinations. In the automotive industry, it is well known that the oxygen concentration in the automobile exhaust has a direct relationship to the engine air-to-fuel ratio. Oxygen gas sensors are employed within the automobile internal combustion control system to provide accurate exhaust gas oxygen concentration measurements for determination of optimum combustion conditions, maximization of efficient fuel usage, and management of exhaust emissions.

Generally, the electrochemical type of oxygen sensor employed in automotive applications utilizes a thimble shaped electrochemical galvanic cell to determine, or sense, the relative amounts of oxygen present in the exhaust stream, an example being U.S. Pat. No. 3,844,920 to Burgett et al. This type of oxygen sensor is generally known and used throughout the automotive industry, and comprises an ionically conductive solid electrolyte material, typically yttria stabilized zirconia, a porous electrode coating on the exterior exposed to the exhaust or measuring gas and a porous electrode coating on the interior exposed to a known concentration of reference gas. The gas concentration gradient across the solid electrolyte produces a galvanic potential which is related to the differential of the partial pressures of the gas at the two electrodes by the Nernst equation: $E = AT \ln[P_1/P_2]$, where E is the galvanic voltage, T is the absolute temperature of the gas, $P_1/P_2$ is the ratio of the partial pressures of the reference gas at the two electrodes, and $A = R/4F$, where R is the universal gas constant and F is the Faraday constant. Thus, the oxygen sensor senses the oxygen concentration in the exhaust gas by measuring this galvanic output voltage.

However, the solid electrolyte of such a sensor must first be heated to an elevated temperature in order to obtain an appreciable output voltage in response to the difference in the oxygen concentrations between the reference and measuring electrodes. The induced galvanic potential between electrodes and corresponding output voltage are not stable until the solid electrolyte has been heated to a given temperature. The combustion gases heat the solid electrolyte of the oxygen sensor to an operating temperature sufficient to effect galvanic stability. Effective sensor operation is therefore delayed until the combustion gases heat the sensor to a suitable temperature.

In addition, if the sensor is placed too far downstream in the exhaust pipe of an engine, especially a highly efficient engine, the sensor may not be heated to a high enough temperature during engine idle to meet sensor specifications. During these conditions, the internal combustion engine control system operates open loop, i.e., the control system does not sense the controlled parameter, air-to-fuel ratio, in order to control that parameter. It is known that a large percentage of the total emissions produced during short period of operation are produced during this period, engine warm up. In some applications, emissions control during engine warm up might be improved with an oxygen sensor which had means for rapidly heating itself to a predetermined temperature, regardless of the temperature of the surrounding environment. Also desirable about an oxygen sensor of this type is that it could be placed anywhere in the exhaust pipe, even at the cooler exit end, since the solid electrolyte of the sensor would not be dependent on the heat of the combustion gases for heat.

Sensor galvanic output voltage is dependent on temperature, as evidenced by the above recitation of the Nernst equation. Temperatures of the combustion gases from an internal combustion engine vary widely during operation, up to about a few hundred degrees Centigrade. Generally, these temperature variations after engine warm up are not detrimental to satisfactory operation of the typical oxygen sensor in use today. Currently, the oxygen sensors are employed in the exhaust gas system of an internal combustion engine to determine qualitatively whether the engine is operating at either of two conditions: (1) a fuel rich or (2) a fuel lean condition, as compared to stoichiometry. After equilibration, the exhaust gases from these two operating conditions have two widely different oxygen partial pressures, varying greatly in magnitude. At these conditions, the output voltage, as determined by the Nernst equation, is greatly dependent on the oxygen partial pressure ratios, yet relatively independent of temperature. Therefore, the typical oxygen sensor in use today does not require strict temperature control during operation.

However, for various reasons, it may be desired to operate internal combustion engines exclusively within lean combustion conditions, i.e., air-to-fuel ratios between 15:1 and 25:1, where changes in the after-combustion oxygen partial pressures are only gradual and slight. At these conditions, the output voltage is greatly dependent on temperature. Temperature control is critical for successful sensing of the exhaust emissions. The stoichiometric oxygen sensors commonly used today are inadequate for these purposes. Also, internal combustion engines operating exclusively within lean combustion conditions operate at cooler temperatures which may not be sufficient to adequately heat the solid electrolyte of the conventional oxygen sensor to its specified operating temperature.

Many heated oxygen sensors have been previously proposed in the art. These prior heated oxygen sensors generally comprise an elongated ceramic heater which positively heats the solid electrolyte body of the sensor. The heater element is typically inserted into an elongated cylindrical hole formed in the solid electrolyte body. An example of a prior heated oxygen sensor of this type is U.S. Pat. No. 4,578,174 to Kato et al.

For automotive applications particularly, a heated oxygen sensor should be rugged, reliable, and readily manufacturable at a low cost. It is also desirable that the heater components be readily adaptable to the current oxygen sensor design and manufacturing techniques. The present invention describes a novel concept for packaging a heated oxygen sensor with a ceramic rod heater. This heated oxygen sensor is easy to fabricate, can be built at minimal cost, and provides a rugged, reliable sensor assembly. It involves initially forming a self aligning heater subassembly comprising an elongated ceramic heater and a gripping body. The heater subassembly is also ruged and reliable, yet simple and amenable to mass production. Further the subassembly is Airedale incorporated into conventional unheated oxygen sensors typified by the above mentioned U.S. Pat. No. 3,844,920 to Burgett et al.

SUMMARY OF THE INVENTION

It is an object of the present invention to provide an improved heated solid electrolyte electrochemical oxygen sensor, the improved heated oxygen sensor being durable and reliable in operation even in comparatively varying environmental conditions. It is a further object of this invention that such improved heated oxygen sensor have a self aligning heater subassembly rigidly secured in an elongated bore formed in a solid electrolyte body, the heater subassembly also capable of electrically communicating the galvanic output signal to the external combustion control system. It is still a further object of this invention that such improved heated oxygen sensor be adaptable to conventional unheated oxygen sensor technology and readily amenable to automotive production techniques.

In accordance with the preferred embodiment of this invention, these and other objects and advantages are accomplished as follows.

According to the present invention, there is provided a heated oxygen sensing device suitable for detecting oxygen concentrations in automotive exhaust emitted from an internal combustion engine. The oxygen sensing device comprises a solid electrolyte body, a housing, an elongated heater element, and self aligning means for rigidly securing and centering the elongated heater element within the solid electrolyte body. The solid electrolyte body is substantially tubular and has an elongated bore located axially, with a first end closed by the solid electrolyte body and a second end open. A reference electrode is provided on the inner surface of the solid electrolyte body. A measuring electrode which contacts the exhaust gas to be measured is provided on the outer surface of the solid electrolyte body. The housing supports the solid electrolyte body so that the measuring electrode on the outer surface of the solid electrolyte body contacts the exhaust gas, while the reference electrode on the inner surface of the solid electrolyte body is gas tight to the external exhaust gas. The elongated heater element is inserted into the elongated bore within the solid electrolyte body. The heater element and solid electrolyte body are securely positioned so that a gap is provided everywhere therebetween the solid electrolyte body and elongated heater element. The elongated heater element comprises a heating resistor having a positive temperature coefficient of resistance and a ceramic body carrying the heating resistor.

According to a preferred aspect of this invention, the means for rigidly securing and centering the heater element within the solid electrolyte body also communicates the galvanic output signal to the external electronic measuring equipment, and comprises a stop body and a gripping body. The stop body has a first end and a second end, the first end being a tubular extension. The second end is shaped to adapt to the housing and does not constitute an inventive feature of this invention. The gripping body has a plurality of outwardly biased semicylindrical rings positioned on a spine from a first end to a second end of the spine. The semicylindrical rings each have a crown of outwardly flared tangs. The semicylindrical rings yieldably encircle the heater element and provide a friction fit therebetween. A U-shaped terminal post having a stop surface is located at a first end of the spine. The U-shaped terminal post extends perpendicularly outward from the spine in a direction opposite of the semicylindrical rings, and may be welded, or otherwise suitably attached, to an electric signal wire for communicating the galvanic output signal generated between the reference and measuring electrodes to the external electronic measuring equipment.

The elongated heater element is inserted within the gripping body to form a heater subassembly. A friction fit between the heater element and gripping body secures the heater element within the gripping body. The stop body is secured to the housing so that the U-shaped terminal post of the gripping body abuts against a first end of the stop body when the heater subassembly is inserted into the elongated bore of the solid electrolyte body. The gripping body, which is of slightly larger diameter than the stop body, must further compress around the heater element when the heater subassembly is inserted into the stop body, rigidly securing the heater element in all directions, and providing an interference fit between the crowns of outwardly flared tangs and the stop body. The outwardly flared tangs on the semicylindrical rings of the gripping body contact the stop body in such a manner so as to rigidly secure and center the heater subassembly within the solid electrolyte body, while also preventing any reverse movement of the heater subassembly. The gripping body also provides the means for electrically communicating the galvanic output signal generated between the reference and measuring electrodes to the external electronic measuring equipment.

Other objects and advantages of this invention will be better appreciated from the following detailed description.

DETAILED DESCRIPTION OF THE INVENTION

This invention produces a heated, solid electrolyte, electrochemical oxygen sensing device suitable for detecting oxygen partial pressures of exhaust gases emitted from an internal combustion engine, which is rugged, reliable, readily assembleable, and amenable to automotive production techniques.

Figure 1:
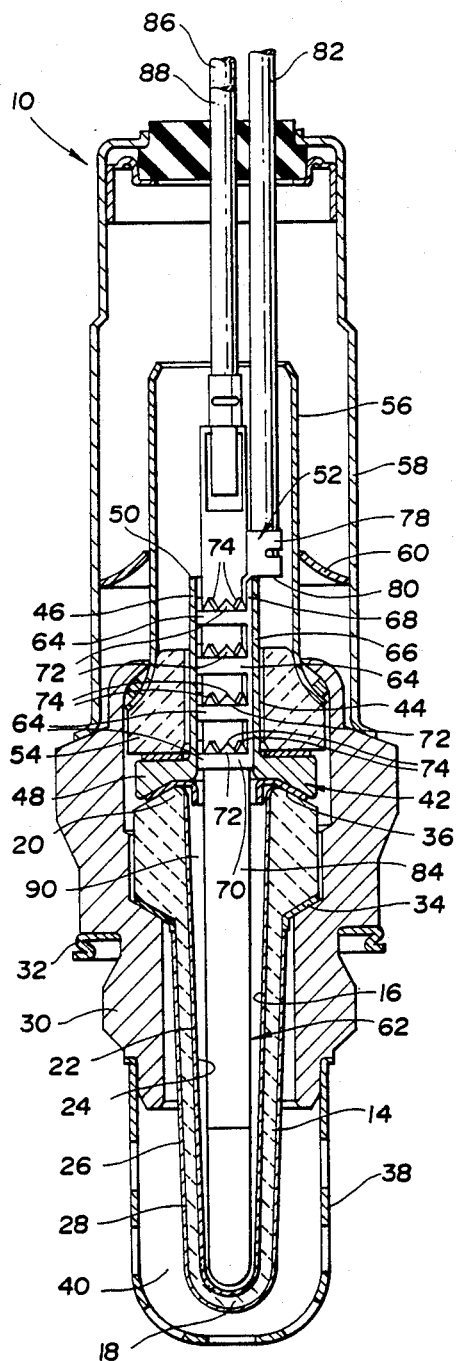
FIG. 1 is a cross sectional view of a heated solid electrolyte oxygen sensor in accordance with a preferred embodiment of this invention and illustrates the solid electrolyte body, housing, heater element, gripping body having a plurality of semicylindrical rings with outwardly flared tangs and U-shaped terminal post, and the stop body.
Figure 4:
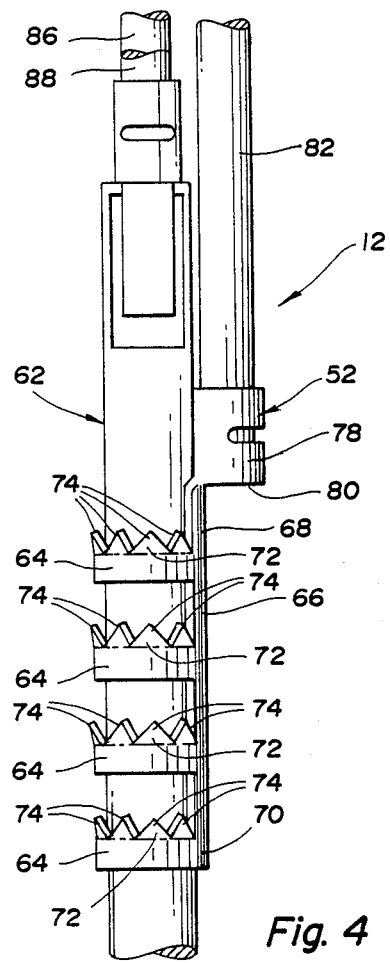
FIG. 4 is an enlarged cross sectional view of the heater subassembly in accordance with a preferred embodiment of this invention as shown in FIG. 1, illustrating the heater element and gripping body.

In the preferred embodiment of this invention, the heated oxygen sensing device 10, as shown in FIG. 1, comprises a heater subassembly 12, as shown in FIG. 4, within an oxygen sensing device. The solid electrolyte body 14 comprises yttria stabilized zirconia and is substantially tubular having an elongated bore 16 located axially. The first end 18 of the solid electrolyte body 14 is closed by the solid electrolyte material. The second end 20 of the solid electrolyte body 14 is open, so that the heater subassembly 12 may be inserted into the elongated bore 16 of the solid electrolyte body 14. A reference electrode 22, preferably comprising porous platinum, is provided on the inner surface 24 of the solid electrolyte body 14 in the elongated bore 16 and contacts a known concentration of reference gas. A measuring electrode 26, preferably comprising porous platinum, is provided on the outer surface 28 of the solid electrolyte body 14 and contacts the exhaust gas to be measured.

The housing 30 is adapted to fit into the exhaust pipe of the automobile, partially shown in FIG. 1 by the mounting plates 32. The housing 30 supports the solid electrolyte body 14 so that the measuring electrode 26 on the outer surface 28 of the solid electrolyte body 14 contacts the external exhaust gas to be measured, while keeping the reference electrode 22 on the inner surface 24 of the solid electrolyte body 14 gas tight to the external exhaust gas. The solid electrolyte body 14 is mounted so as to resemble a finger-like projection into the flow of exhaust gases. Lower and intermediate gaskets 34 and 36, respectively, seal the elongated bore 16 of the solid electrolyte body 14 and prevent flow of the external exhaust gas into the elongated bore 16 of the solid electrolyte body 14 where the reference electrode 22 is provided. A perforated shield 38 is attached to the housing 30 and provides protection for the solid electrolyte body 14. A gap 40 is provided between the perforated shield 38 and solid electrolyte body 14 to allow uninterrupted flow of the exhaust gases through the perforated shield 38 to the porous platinum measuring electrode 26 on the outer surface 28 of the solid electrolyte body 14.

A stop body 42 having a tubular extension 44 at a first end 46 of the stop body 42 is concentric with the elongated bore 16 of the solid electrolyte body 14. The second end 48 of the stop body 42 is shaped to adapt to the intermediate gasket 36 and does not constitute an inventive feature of this invention. The first end 46 of the stop body 42 provides a seat 50, or abutment surface, for the gripping body 52, which will be discussed fully further in the detailed description of this preferred embodiment. The stop body 42 may be formed from any suitable material, preferably a 400 series stainless steel.

An alumina insulator 54 is positioned by the stop body 42 and insulates the metal stop body 42 from the housing 30 or inner upper shield 56, which are both also preferably formed from a metal. The galvanic output signal generated between the reference and measuring electrodes 22 and 26, flows through the intermediate gasket 36, stop body 42, and gripping body 52; therefore the alumina insulator 54 is required to prevent electrical communication of this output signal to the housing 30 or inner upper shield 56.

An outer upper shield 58 is held by a spring clip 60, or other suitable means, to the inner upper shield 56. The outer upper shield 58 and inner upper shield 56 provide additional protection for the heated oxygen sensor 10 and may be formed from a suitable material.

The heater subassembly 12, which is readily adaptable to conventional unheated oxygen sensor design, as shown in FIG. 4, comprises a gripping body 52 and elongated heater element 62. An inventive feature of the present invention is the gripping body 52, enlarged and isolated in FIGS. 2 and 3. The gripping body 52 has a plurality of outwardly biased semicylindrical rings 64 positioned on a spine 66 from a first end 68 to a second end 70 of the spine. In the preferred embodiment there are four semicylindrical rings 64 provided, although more or less may be provided, so long as the heater element 62 is secured rigidly in all directions of movement, axially, radially, and orbitally, when inserted into the elongated bore 16 of the solid electrolyte body 14.

Figure 3:
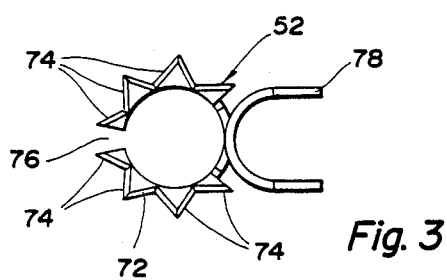
FIG. 3 is a top view of the gripping body shown in FIG. 2.

The semicylindrical rings 64 each have a crown 72 of outwardly flared tangs 74. Preferably, the tangs 74 are flared outward at about 45 degrees, to optimize both the horizontal and vertical force components exerted when the gripping body 52 is inserted into the stop body 42. The semicylindrical rings 64 are discontinuous in their cylindrical form (76), as shown in FIG. 3. The semicylindrical rings 64 yieldably encircle the heater element 62 when the heater element 62 is inserted thereto, and provide a friction fit therebetween. The discontinuity 76 in the semicylindrical rings 64 permits the gripping body 52 to further compress around the heater element 62 when the heater subassembly 12 is inserted into the stop body 42 of the oxygen sensor 10. The gripping body 52 is preferably fabricated from a 400 series stainless steel, however any suitable material may be used.

An alternative embodiment of the gripping body comprises a single outwardly biased semicylindrical ring having a plurality of outwardly flared tangs, instead of the plurality of outwardly biased semicylindrical rings each having a crown of outwardly flared tangs, as disclosed in the preferred embodiment. The single semicylindrical ring is tubular and has a plurality of outwardly flared tangs provided throughout its structure. The outwardly flared tangs are formed in the semicylindrical tube by punching or other suitable means.

Figure 2:
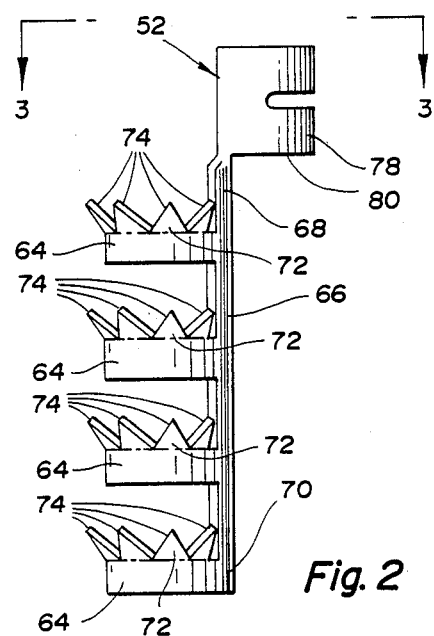
FIG. 2 is a side elevational view of the gripping body in accordance with a preferred embodiment of this invention.

A U-shaped terminal post 78 having a stop surface 80 is located at a first end 68 of the gripping body spine 66, shown enlarged in FIGS. 2 and 3. The U-shaped terminal post 78 extends perpendicularly outward from the spine 66 in a direction opposite of the semicylindrical rings 64, and may be crimped and welded, or otherwise suitably attached, to an electronic output signal wire 82 for communicating the galvanic output signal generated between the reference and measuring electrodes 22 and 26, respectively, to the external electronic measuring equipment, not shown. An advantage of the present invention, is that the U-shaped terminal post 78 not only provides the stop surface 80 for locating and centering the heater subassembly 12 within the solid electrolyte body 14, as will be discussed fully later, but also the means for electrically coupling the galvanic output signal generated by the reference and measuring electrodes 22 and 26, respectively, to the external measuring equipment, not shown.

The elongated heater element 62 is inserted within the gripping body 52 to form the heater subassembly 12, as shown in FIG. 4. The heater element 62 is electrically connected to a heater power wire 86 and ground wire 88. The elongated heater element 62 comprises a heating resistor, not shown, having a positive coefficient of resistance embedded in a ceramic core 84. The heater element 62 employed may be a commercially available type, such as a circular, elongated rod comprising an alumina core, tungsten wires, and insulating overlayer.

An advantageous feature of the gripping body 52 is that non-circular heater element rods 62 may also be used, such as an elongated, rectangular shaped rod comprising an alumina core, platinum wires, and insulating overlayer, or an elongated triangular shaped heater element, so long as the desired configuration permits the gripping body 52 to yieldably encircle and contact the heater element 62. An advantage of utilizing a non-circular shaped heater element 62 is that the gripping body 52 only contacts the heater element 62 at a fixed number of points, permitting greater air flow between the gripping body 52 and heater element 62, which in turn provides a greater reference oxygen gas source to the reference electrode 22 on the inner surface 24 of the solid electrolyte body 14. This aspect of the present invention provides some flexibility in the heated oxygen sensor design, a desirable feature for any component in the automotive industry.

A friction fit between the heater element 62 and semicylindrical rings 64 of the gripping body 52 secures the heater element 62 within the semicylindrical rings 64 when the heater element 62 is inserted thereto. The heater element 62 is positioned within the gripping body 52 so that an appropriate length of the heater element 62 projects into the elongated bore 16 of the solid electrolyte body 14 when the heater subassembly 12 is inserted into the elongated bore 16 of the solid electrolyte body 14. A gap 90 is desired everywhere between the heater element 62 and solid electrolyte body 14 in order to ensure a constant reference oxygen source to the reference electrode 22 and also to prevent any detrimental overheating of the solid electrolyte body 14 or porous platinum reference electrode 22. Alternatively, it is also desirable to optimally minimize the gap 90 between the heater element 62 and solid electrolyte body 14 in order to quickly achieve uniform heating throughout the solid electrolyte body 14.

The heater subassembly 12, comprising the gripping body 52, heater element 62, output signal wire 82, heater power wire 86, and ground wire 88, is inserted into the stop body 42 which is secured in the housing 30, so that the heater element 62 protrudes into the elongated bore 16 of the solid electrolyte body 14. As the heater subassembly 12 is inserted in the stop body 42, the stop surface 80 of the gripping body 52 U-shaped terminal post 78 abuts against the seat 50 at the first end 46 of the stop body 42, axially and concentrically positioning the heater subassembly 12 within the elongated bore 16 of the solid electrolyte body 14.

An interference fit between the stop body 42 and outwardly flared tangs 74 of the gripping body 52, which are of slightly larger diameter than the stop body 42, rigidly secures and centers the heater subassembly 12 within the stop body 42. Due to the diametral differences, the discontinuity 76 in the outwardly biased semicylindrical rings 64 of the gripping body 52 permit further compression of the semicylindrical rings 64 around the heater element 62, rigidly securing the heater element 62 in all directions, axially, radially, and orbitally. The outwardly flared tangs 74 on the semicylindrical rings 64 of the gripping body 52 contact the stop body 42 so as to rigidly secure and center the entire heater subassembly 12 within the elongated bore 16 of the solid electrolyte body 14, while also preventing any reverse movement of the heater subassembly 12 within the solid electrolyte body 14.

In the preferred embodiment, the outwardly flared tangs 74 on the semicylindrical rings 64 of the gripping body 52 point upward, i.e., the vertical component of the outward flare points toward the direction of the first end 68 of the gripping body 52 or toward the first end 46 of the stop body 42 when inserted thereto. The outwardly flared tangs 74 could also be oppositely pointed downward, i.e., the vertical component of the outward flare points toward the second end 70 of the gripping body 52 or second end 48 of the stop body 42, without detrimental effects. However, this downward configuration would prove more difficult during assembly of the heater subassembly 12 within the stop body 42.

In the preferred embodiment, the gripping body 52 also provides the means for electrically coupling the galvanic output signal generated between the reference and measuring electrodes 22 and 26, respectively, to the external electronic measuring equipment, not shown. The electrical current generated by the galvanic potential across the solid electrolyte body 14 between the reference and measuring electrodes 22 and 26, flows through the intermediate gasket 36, stop body 42, and U-shaped terminal post 78 of the gripping body 52 to the output signal wire 82. The output signal wire 82 leads to external measuring equipment, not shown. The gripping body 52, therefore, not only provides a simple and efficient manner in which to align and secure a heater element 62 within an unheated oxygen sensor assembly, but also provides the means for electrically coupling the galvanic output signal with the external electronic combustion control system.

A desirable feature of the present invention is its amenability to automotive mass production techniques. The heater subassembly 12 is relatively easy to assemble and may be utilized in conventional unheated oxygen sensors without much modification of the conventional design. The heater subassembly 12 when installed in the stop body 42 of the housing 30 is self aligning and rigidly secured in all directions of movement. Further the heater subassembly 12, particularly the gripping body 52, provides the means for electrically communicating the galvanic output signal to the external electronic measuring equipment, therefore minimizing the number of components in the heated oxygen sensing device 10.

While our invention has been described in terms of a preferred embodiment, it is apparent that other forms could be adopted by one skilled in the art. Accordingly, the scope of our invention is to be limited only by the following claims.

The embodiments of the invention in which an exclusive property or privilege is claimed are defined as follows:

1. An oxygen sensing device, comprising:
   a substantially tubular solid electrolyte body having an elongated bore axially located, with a first end closed by said solid electrolyte and a second end open, said solid electrolyte body having a reference electrode provided on an inner surface thereof and a measuring electrode provided on an outer surface thereof;
   a housing, said housing supports said solid electrolyte body so that said measuring electrode of said solid electrolyte body contacts the external gas to be measured and so that said reference electrode of said solid electrolyte body is gas tight to the external gas to be measured;
   an elongated heater element comprising a heating resistor having a positive coefficient of resistance, said elongated heater element being inserted within said elongated bore of said solid electrolyte body;

a gripping body having a spine, at least one outwardly biased semicylindrical ring positioned on said spine from a first end to a second end of said spine, and a terminal post having a stop surface, said semicylindrical ring having a plurality of outwardly flared tangs, further said semicylindrical ring yieldably encircles said heater element to provide a friction fit therebetween, said terminal post located at said first end of said spine and extending outward from said semicylindrical ring; and a stop body having a seat for said terminal post of said gripping body, so that said stop surface of said terminal post abuts against said first end of said stop body and so that said plurality of outwardly flared tangs contact an inner diameter of said stop body when said gripper body encircling said heater element is inserted within said stop body, said stop body provided within said housing body.

2. An oxygen sensing device according to claim 1, wherein said elongated heater element is a circular rod comprising an alumina core, tungsten wires, and an insulating overlayer.

3. An oxygen sensing device according to claim 1, wherein said elongated heater element is a rectangular rod comprising an alumina core, platinum wires, and an insulating overlayer.

4. An oxygen sensing device, comprising:
a substantially tubular solid electrolyte body having an elongated bore centrally and axially located, with a first end closed by said solid electrolyte material and a second end open, said solid electrolyte body having a reference electrode provided on an inner surface thereof and a measuring electrode provided on an outer surface thereof;

a housing, said housing supports said solid electrolyte body so that said measuring electrode of said solid electrolyte body contacts the external exhaust gas to be measured and so that said reference electrode of said solid electrolyte body is gas tight to the external exhaust gas to be measured;

an elongated heater element comprising a heating resistor having a positive coefficient of resistance, said elongated heater element being inserted within said elongated bore of said solid electrolyte body;

a gripping body having a spine, at least one outwardly biased generally semicylindrical ring positioned on said spine from a first end to a second end of said spine, and a U-shaped terminal post having a stop surface, said semicylindrical ring having a plurality of outwardly flared tangs, further, said semicylindrical ring yieldably encircles said heater element to provide a friction fit therebetween, said U-shaped terminal post being located at said first end of said spine and extending perpendicularly outward from said semicylindrical ring for electrically connecting to an electric signal wire; and a stop body having a tubular extension at a first end which provides a seat for said U-shaped terminal post of said gripping body, so that said stop surface of said U-shaped terminal post abuts against said first end of said stop body and so that said plurality of outwardly flared tangs contact an inner diameter of said stop body when said gripper body encircling said heater element is inserted within said stop body, said stop body provided within said housing body;

effective to (1) rigidly secure and center said elongated heater element within said solid electrolyte body so that a gap exists everywhere therebetween said heater element and said solid electrolyte body, and (2) electrically communicate the galvanic output signal generated between said reference electrode and said measuring electrode to external electronic measuring equipment.

5. An oxygen sensing device according to claim 4, wherein there is a single semicylindrical ring, which is tubular, having a plurality of outwardly flared tangs.

6. An oxygen sensing device according to claim 4, wherein the number of said semicylindrical rings is four, each ring having a crown of outwardly flared tangs.

7. An oxygen sensing device according to claim 4, wherein said elongated heater element is a circular rod comprising an alumina core, tungsten wires, and an insulating overlayer.

8. An oxygen sensing device according to claim 4, wherein said elongated heater element is a rectangular rod comprising an alumina core, platinum wires, and an insulating overlayer.

9. A device for rigidly securing and centering a heater element within a heated oxygen sensor which is self aligning, comprising:
a spine;
at least one outwardly biased semicylindrical ring positioned on said spine from a first end to a second end of said spine for yieldably encircling a heater element and securing with a friction fit therebetween, said semicylindrical ring having a plurality of outwardly flared tangs; and
a terminal post having a stop surface, said terminal post located at said first end of said spine and extending outward from said semicylindrical rings.

* * * * *